(12) United States Patent
Sasaki

(10) Patent No.: US 9,283,169 B2
(45) Date of Patent: Mar. 15, 2016

(54) WATER-IN-OIL EMULSIFIED SKIN COSMETIC

(71) Applicant: Shiseido Company, Ltd., Tokyo (JP)

(72) Inventor: Kazutaka Sasaki, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 16 days.

(21) Appl. No.: 14/365,304

(22) PCT Filed: Dec. 10, 2012

(86) PCT No.: PCT/JP2012/081926
§ 371 (c)(1),
(2) Date: Jun. 13, 2014

(87) PCT Pub. No.: WO2013/108515
PCT Pub. Date: Jul. 25, 2013

(65) Prior Publication Data
US 2014/0348765 A1    Nov. 27, 2014

(30) Foreign Application Priority Data

Jan. 16, 2012   (JP) ................................. 2012-005760

(51) Int. Cl.

| A61K 8/891 | (2006.01) |
|---|---|
| A61K 8/27 | (2006.01) |
| A61K 8/29 | (2006.01) |
| A61K 8/31 | (2006.01) |
| A61K 8/34 | (2006.01) |
| A61K 8/894 | (2006.01) |
| A61K 8/37 | (2006.01) |
| A61K 8/58 | (2006.01) |
| A61K 8/06 | (2006.01) |
| A61K 8/04 | (2006.01) |
| A61K 8/19 | (2006.01) |
| A61Q 17/04 | (2006.01) |
| A61Q 1/02 | (2006.01) |

(52) U.S. Cl.
CPC . *A61K 8/891* (2013.01); *A61K 8/04* (2013.01); *A61K 8/064* (2013.01); *A61K 8/19* (2013.01); *A61K 8/27* (2013.01); *A61K 8/29* (2013.01); *A61K 8/31* (2013.01); *A61K 8/34* (2013.01); *A61K 8/37* (2013.01); *A61K 8/585* (2013.01); *A61K 8/894* (2013.01); *A61Q 1/02* (2013.01); *A61Q 17/04* (2013.01); *A61K 2800/40* (2013.01)

(58) Field of Classification Search
CPC ............ A61K 8/27; A61K 8/29; A61K 8/31; A61K 8/34; A61K 8/891; A61K 8/064; A61K 8/04; A61K 8/19; A61K 8/37; A61K 8/585; A61K 8/894; A61K 2800/40
See application file for complete search history.

(56) References Cited

U.S. PATENT DOCUMENTS

| 2010/0190871 A1 | 7/2010 | Araki et al. |
|---|---|---|
| 2010/0310496 A1* | 12/2010 | Iimura ................... A61K 8/898 424/78.17 |
| 2011/0135585 A1* | 6/2011 | Ikeda ....................... A61K 8/06 424/70.7 |
| 2012/0301523 A1 | 11/2012 | Fukui et al. |

FOREIGN PATENT DOCUMENTS

| EP | 2 174 985 A1 | 4/2010 |
|---|---|---|
| EP | 2 180 028 A1 | 4/2010 |
| EP | 2 314 280 A1 | 4/2011 |
| JP | 2002080771 A | 3/2002 |
| JP | 2009084232 A | 4/2009 |
| JP | 2010143844 A | 7/2010 |
| WO | 2008/046762 A1 | 4/2008 |
| WO | 2009025146 A1 | 2/2009 |
| WO | 2010016437 A1 | 2/2010 |
| WO | WO 2010/016437 * | 2/2010 |
| WO | 2011065438 A1 | 6/2011 |
| WO | 2012070309 A1 | 5/2012 |

OTHER PUBLICATIONS

JP 2009084232 A, using Eng. Abstract, Apr. 23, 2009.*
The International Bureau of WIPO, "Notification of Transmittal of Translation of the International Preliminary Report on Patentability," issued in International Application No. PCT/JP2012/081926, of which U.S. Appl. No. 14/365,304 is a U.S. national phase entry, with a date of mailing of Jul. 31, 2014.
European Patent Office, "Extended European Search Report," issued in European Patent Application No. 12 866 160.0, which is a European Counterpart of U.S. Appl. No. 14/365,304, with an issuance date of Jul. 1, 2015, 4 pages.
* cited by examiner

*Primary Examiner* — Blessing M Fubara

(57) ABSTRACT

The present invention relates to a water-in-oil emulsified skin cosmetic comprising the following ingredients (a) through (e):
(a) Water: 5-50 wt %
(b) Ethanol: 1-20 wt %
(c) Volatile oil component: 2-50 wt %
(d) Carboxy decyl trisiloxane represented by the following formula (1): 0.1-5 wt %

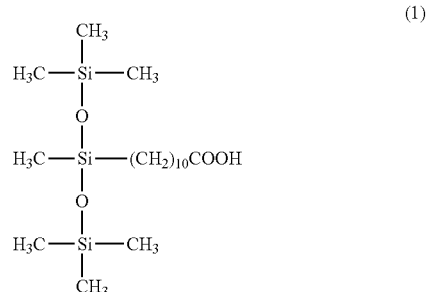

(1)

(e) One, two or more selected from a group consisting of hydrophobized titanium dioxide, hydrophobized zinc oxide, and hydrophobized iron oxide: 2-50 wt %;
wherein the object of the present invention is to provide a water-in-oil emulsified skin cosmetic containing the aforementioned powder (e) wherein powdery squeakiness over time after application on the skin is suppressed and at the same time absorption into the skin at the time of application and the absence of stickiness after application on the skin are improved.

4 Claims, No Drawings

WATER-IN-OIL EMULSIFIED SKIN COSMETIC

CROSS REFERENCE TO RELATED APPLICATIONS

This patent application is a U.S. national stage application under 35 U.S.C. §371 of International Patent Application No. PCT/JP2012/081926 filed on Dec. 10, 2012, which claims the benefit of foreign priority to Japanese Patent Application No. JP 2012-005760 filed on Jan. 16, 2012, the disclosures of all of which are hereby incorporated by reference in their entireties. The International Application was published in Japanese on Jul. 25, 2013, as International Publication No. WO 2013/108515 A1 under PCT Article 21(2).

TECHNICAL FIELD

The present invention relates to a water-in-oil emulsified skin cosmetic. More specifically, it relates to a water-in-oil emulsified skin cosmetic into which one, two, or more powders selected from a group consisting of hydrophobized titanium dioxide, hydrophobized zinc oxide, and hydrophobized iron oxide, are blended wherein powdery squeakiness on the skin over time after application is suppressed, absorption into the skin at the time of application is improved, and the absence of stickiness after application on the skin is improved.

BACKGROUND ART

Patent Document 1 discloses a cosmetic that is a pigment dispersion containing the pigments composed of titanium dioxide and/or zinc oxide and a dispersion solvent composed of liquid oil and a dispersing agent wherein a specific reactive organically-modified silicone is used for the dispersing agent. As a result, this is a cosmetic that manifests effects such as good spreadability of the cosmetic, an improvement in transparency of the coating film, absence of powderiness, and absence of unnatural whiteness.

The reactive organically-modified silicone used in Patent Document 1 includes amino-modified silicone and/or carboxy-modified silicone; specifically, a reactive organically-modified silicone that has a higher molecular weight than that of carboxy decyl trisiloxane used in the invention of the present application. Therefore a formulation of said cosmetic has a high viscosity, and a uniform coating film may not be obtained when applied on the skin.

Also, when the liquid oil evaporates over time, the pigment in the coating film of said cosmetic lacks fluidity and therefore the powdery squeakiness of the pigment cannot be solved effectively.

On the other hand, Patent Document 2 reports an invention that uses carboxy decyl trisiloxane, which is a carboxy-modified silicone used in the invention of the present application.

However, the invention of Patent Document 2 relates to "a method for producing a powder cosmetic from dried powder that includes a slurry preparation process for mixing a powder component with a nonvolatile oil-based component as a binder and a carboxylic acid-modified silicone as a dispersant in a volatile solvent to give a slurry and a drying process for drying the slurry to give dry powder wherein the dryer used in the drying process is a dryer that finely forms the slurry into droplets by a mechanical shear force and sends a dry gas to the fine droplets to dry the slurry" and it is an invention that provides a preparation method to prepare a powder cosmetic superior particularly in terms of long lasting coverage; it is an invention with a completely different content compared with the invention of the present application.

PRIOR ART DOCUMENTS

Patent Documents

Patent Document 1: JP 2002-80771 A
Patent Document 2: JP 2010-143844 A

DISCLOSURE OF INVENTION

Technical Problem

The inventor of the invention of the present application discovered that, by selecting carboxy decyl trisiloxane having a specific structure from carboxy-modified silicones and blending a specific amount of carboxy decyl trisiloxane, a specific amount of water, a specific amount of ethanol, and a specific amount of a volatile oil component into a water-in-oil emulsified skin cosmetic containing powder such as titanium dioxide, zinc oxide, and iron oxide, which are often used in cosmetics, powdery squeakiness over time after application on the skin could be suppressed and absorption into the skin at the time of application and the absence of stickiness after application on the skin could be improved, thus completing the present invention.

The object of the present invention is to provide a water-in-oil emulsified skin cosmetic into which one, two, or more powders selected from a group consisting of titanium dioxide, zinc oxide, and iron oxide, are blended wherein powdery squeakiness (tactile sensation of a lack of smoothness) on the skin over time after application is suppressed, absorption into the skin at the time of application is improved, and the absence of stickiness after application on the skin is improved.

Technical Solution

That is, the present invention provides a water-in-oil emulsified skin cosmetic comprising the following ingredients (a) through (e):
(a) Water: 5-50 wt %
(b) Ethanol: 1-20 wt %
(c) Volatile oil component: 2-50 wt %
(d) Carboxy decyl trisiloxane represented by the following formula (I): 0.1-5 wt %

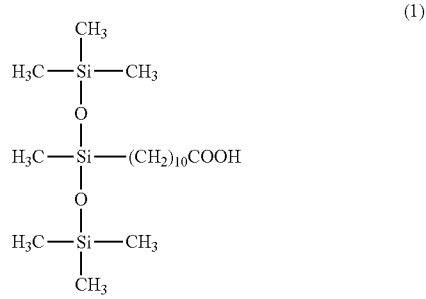

(e) One, two or more selected from a group consisting of hydrophobized titanium dioxide, hydrophobized zinc oxide, and hydrophobized iron oxide: 2-50 wt %.

In addition, the present invention provides the aforementioned water-in-oil emulsified skin cosmetic wherein (f) polyether-modified silicone is used for emulsification of said water-in-oil emulsified skin cosmetic.

Furthermore, the present invention provides the aforementioned water-in-oil emulsified skin cosmetic that additionally contains (g) an ultraviolet absorbent.

Advantageous Effects of the Invention

According to the present invention, it is possible to provide a water-in-oil emulsified skin cosmetic into which powder commonly used in cosmetics such as hydrophobized titanium dioxide, zinc oxide, and iron oxide, is blended wherein powdery squeakiness on the skin over time after application is suppressed and a squeaky sensation is absent.

Also, according to the present invention, it is possible to provide a water-in-oil emulsified skin cosmetic into which powder commonly used in cosmetics such as hydrophobized titanium dioxide, zinc oxide, and iron oxide, is blended wherein absorption into the skin at the time of application and the absence of stickiness on the skin after application are improved.

BEST MODE FOR CARRYING OUT THE INVENTION

The present invention is described in detail below.

"(a) Water"

Selection of water to be blended in is not limited in particular; ion-exchanged water is preferably used.

In the present invention, water, along with other water-based ingredients, constitutes the water phase, which is the inner phase of the water-in-oil emulsified skin cosmetic.

The blend ratio of water is 5-50 wt %, preferably 6-40 wt %, of the total amount of the water-in-oil emulsified skin cosmetic.

"(b) Ethanol"

In the present invention, ethanol, along with water, constitutes the water phase, which is the inner phase of the water-in-oil emulsified skin cosmetic.

The blend ratio of ethanol is 1-20 wt %, preferably 3-15 wt %, relative to the total amount of the water-in-oil emulsified skin cosmetic.

"(c) Volatile Oil Component"

Examples of the volatile oil component used in the present invention include relatively low molecular weight hydrocarbon oils, relatively low molecular weight straight chain silicones, and relatively low molecular weight cyclic silicones; particularly preferable are light liquid isoparaffin, isododecane, isohexadecane, volatile dimethylpolysiloxane, and cyclic polysiloxane. Specifically, octamethylcyclotetrasiloxane, decamethylcyclopentasiloxane, dodecamethylcyclohexasiloxane, and hexadecamethylcycloheptasiloxane are preferable. Particularly preferable are light liquid isoparaffin, isododecane, isohexadecane, and decamethylcyclopentasiloxane.

The volatile oil component used in the present invention is an ingredient that, along with oil components in other optional ingredients, constitutes the oil phase, i.e., outer phase, of the water-in-oil emulsified skin cosmetic. And, fine powder of the hydrophobized zinc oxide, titanium dioxide, and iron dioxide, i.e., the following ingredient (d), is uniformly dispersed in said oil component in the outer phase.

The blend ratio of the volatile oil component is 2-50 wt %, preferably 5-45 wt %, more preferably 10-40 wt %, of the total amount of the water-in-oil emulsified skin cosmetic.

Selection of the oil component in the optional ingredients constituting the oil phase is not limited in particular; examples include fats and oils, waxes, hydrocarbon oils, plant oils, higher fatty acids, higher alcohols, synthetic esters, and silicone oils. The blend ratio is determined as appropriate for the product; normally 3-20 wt % relative to the total amount of the water-in-oil emulsified skin cosmetic can be blended in.

"(d) Carboxy Decyl Trisiloxane Represented by the Following Formula (I)"

The carboxy-modified silicone used in the present invention is carboxy decyl trisiloxane represented by the following formula (I).

Said ingredient (d) in the present invention is an essential ingredient that is dissolved in the oil phase of the water-in-oil emulsified skin cosmetic and the action of said ingredient suppresses powdery squeakiness of the fine powder of zinc oxide, titanium dioxide, and iron oxide.

{Chemical formula 2}

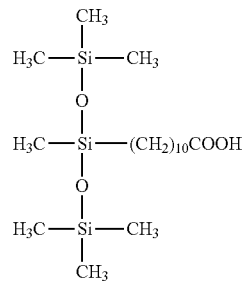

(1)

Its chemical name is 3-(10-carboxydecyl)-1,1,1,3,8,5,5-heptamethyltrisiloxane; it is a prior art carboxy modified silicone. In the present invention, commercial products such as "Dow Corning Toray OP-1800MF Carboxy Fluid (from Dow Corning Toray)" are preferably used.

Carboxy decyl trisiloxane represented by formula (1) is, as described above, a prior art carboxy-modified silicone that is a cosmetic ingredient. However, it has never been blended into a water-in-oil emulsified skin cosmetic containing one, two, or more powders selected from a group consisting of titanium dioxide, zinc oxide, and iron oxide as a cosmetic ingredient that suppresses powdery squeakiness on the skin over time after application. And the effect of the present invention, i.e., suppressing powdery squeakiness over time after application on the skin and at the same time improving absorption into the skin at the time of application and the absence of stickiness after application on the skin by introducing the composition of the present invention, is an unforeseeable significant effect that was discovered by the inventor for the first time.

The blend ratio of the carboxy decyl trisiloxane represented by formula (1) is 0.1-5 wt %, preferably 0.1-3 wt %, more preferably 0.5-2 wt %, relative to the total amount of the water-in-oil emulsified skin cosmetic.

"(e) One, Two or More Selected from a Group Consisting of Hydrophobized Titanium Dioxide, Hydrophobized Zinc Oxide, and Hydrophobized Iron Oxide"

Titanium dioxide and zinc oxide are powders often used in a sunscreen cosmetic as an ultraviolet scattering agent, for example; these powders tend to cause powdery squeakiness after the application of the cosmetic.

Also, iron oxide is a powder often used to improve the skin brightness after application or to improve brightness and color unevenness of the skin after application; it is also a powder that tends to cause powdery squeakiness after the application of the cosmetic.

The aforementioned powders are hydrophobized powders; selection of the hydrophobicizing agent and/or hydrophobicizing method is not limited and the hydrophobicizing treatment is conducted using a prior art hydrophobicizing agent with a conventional method. Examples of the hydrophobicizing agent include silicone treatment agents, fatty acids, fatty acid soaps, and fatty acid esters. Examples of the silicone treatment agent include various silicone oils such as methyl hydrogen polysiloxane, dimethylpolysiloxane, and methylphenylpolysiloxane, various alkylsilanes such as methyltrimethoxysilane, ethyltrimethoxysilane, hexyltrimethoxysilane, and octyltrimethoxysilane, and various fluoroalkylsilanes such as trifluoromethylethyltrimethoxysilane and heptadecafluoromethylethyltrimethoxysilane. Examples of the fatty acid include palmitic acid, isostearic acid, stearic acid, Laurie acid, myristic acid, behenic acid, oleic acid, rosin acid, and 12-hydroxystearic acid. Examples of the fatty acid soap include aluminum stearate, calcium stearate, and aluminum 12-hydroxystearate. Examples of the fatty acid ester include dextrin esters of fatty acids, cholesterol esters of fatty acids, sucrose esters of fatty acids, and starch esters of fatty acids. One, two, or more of these hydrophobicizing agents can be used to conduct a hydrophobicizing treatment of the fine powder following a conventional method.

The hydrophobized fine powder is dispersed uniformly in the oil phase, i.e., the outer phase of the water-in-oil emulsified skin cosmetic of the present invention.

Regarding the aforementioned powder, blending in fine powder having an average particle size of 10-1,000 nm is preferable in view of the ultraviolet protection effect, improvement in color or unevenness improvement in the skin brightness after application. The average particle size is measured with a usual method such as the number average diameter derived from image analysis of electron microscope images, for example.

The blend ratio of the one, two, or more powders selected from a group consisting of titanium dioxide, zinc oxide, and iron oxide is 2-50 wt %, preferably 5-40 wt %, more preferably 7-35 wt % relative to the total amount of the water-in-oil emulsified skin cosmetic.

"(f) Polyether-modified Silicone"

For the surfactant (emulsifying agent) to be used for the water-in-oil emulsified skin cosmetic of the present invention, polyether-modified silicone is preferable.

Selection of the polyether-modified silicone to be used in the present invention is not limited in particular; examples include those containing branched silicone chains and/or alkyl chains. Examples of commercially available polyether-modified silicones include Silicone KF-6017P, Silicone KF-6028, and Silicone KF-6038 from Shin-Etsu Chemical Co., Ltd. as well as ABIL EM 90 from Degussa GmbH.

In the present invention, surfactants (emulsifying agents) other than polyether-modified silicones can be additionally used as long as the effect of the present invention is not adversely affected.

The blend ratio of the polyether-modified silicone is 0.1-10 wt%, preferably 0.5-5 wt %, relative to the total amount of the cosmetic.

"(g) Ultraviolet Absorbent"

It is also preferable to blend an ultraviolet absorbent into the water-in-oil emulsified skin cosmetic of the present invention to use it as a sunscreen cosmetic. In particular, if zinc oxide and/or titanium dioxide, which are ultraviolet scattering agents, are blended in, there is the advantage of increasing the ultraviolet protection effect in addition to ultraviolet absorption.

Examples of ultraviolet absorbents include the following compounds.

(1) Benzoic Acid Ultraviolet Light Absorbents

For example, paraminobenzoic acid (hereafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester.

(2) Anthranilic Acid Ultraviolet Light Absorbents

For example, homo mentyl-N-acetyl anthranilate.

(3) Salicylic Acid Ultraviolet Light Absorbents

For example, amyl salicylate, mentyl salicylate, homo mentyl salicylate, octyl salicylate, phenyl salicylate, benzyl salicylate, and p-isopropanol phenyl salicylate.

(4) Cinnamic Acid Ultraviolet Light Absorbents

For example, octylcinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octytl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl mono-2-ethyl hexanoyl-diparamethoxycinnamate.

(5) Triazine Ultraviolet Light Absorbents

Examples include bisresorsinyl triazine.

More specifically, bis{[4-(2-ethylhexyloxy)-2-hydroxyl]phenyl}-6-(4-methoxyphenyl)-1,3,5-triazine, and 2,4,6-tris{4-(2-ethylhexyloxycarbonyl)-anilino}-1,3,5-triazine.

(6) Other Ultraviolet Light Absorbents

For example, 3-(4'-methylbenzylidene)-d,l-camphor, 3-benzylidene-d,l-camphor, 2-phenyl-5-methyl benzoxazol, 2,2'-hydroxy-5-methylphenyl benzotriazol, 2-(2'-hydroxy-5'-t-octylphenyl) benzotriazol, 2-(2'-hydroxy-5'-methylphenyl benzotriazol), dianisoylmethane, 4-methoxy-4'-t-butyl dibenzoyl-methane, and 5-(3,3-dimethyl-2-norbornylidene)-3-pentane-2-one. Also, pyridazine derivatives such as dimorpholinopyridazinone.

The blend ratio of the ultraviolet absorbent is determined as appropriate for the target product; it is usually 1-25 wt %, preferably 5-20 wt %, relative to the total amount of the water-in-oil emulsified skin cosmetic.

In addition to the aforementioned essential ingredients, other ingredients used in cosmetics can be blended as necessary in the water-in-oil emulsified skin cosmetic of the present invention; examples of such ingredients include humectants, water soluble polymers, thickeners, coating agents, sequestering agents, polyhydric alcohols, sugars, amino acids, organic amines, polymer emulsions, pH adjusting agents, skin nutrients, vitamins, antioxidants, antioxidation assistants, and perfumes, and the water-in-oil emulsified skin cosmetic can be prepared for the target product with a conventional method.

EXAMPLES

The present invention is further described in detail below by referring to Examples. The present invention is not limited to these examples. The blend ratios are in relation to the total amount and in weight-percentage units unless specified otherwise.

Using the formulations shown in Table 1 and Table 2, sunscreen creams that were water-in-oil emulsified skin cosmetics were prepared with a conventional method and an actual use test was conducted by a panel of ten specialists to assess the texture when applied on the face, based on the following criteria.

"Suppression of Powdery Squeakiness of the Powder Ingredient (e) Over Time (Absence of Powdery Squeakiness an Hour after Application on the Skin)"

<Assessment Criteria>
- ⊚: 9-10 reported the absence of powdery squeakiness one hour after the application.
- ◯: 6-8 reported the absence of powdery squeakiness one hour after the application.
- Δ: 3-5 reported the absence of powdery squeakiness one hour after the application.
- Δx: 1-2 reported the absence of powdery squeakiness one hour after the application.
- x: 0 reported the absence of powdery squeakiness one hour after the application.

"Good Absorption into the Skin at the Time of Application"

<Assessment Criteria>
- ⊚: 9-10 reported good absorption into the skin at the time of application.
- ◯: 6-8 reported good absorption into the skin at the time of application.
- Δ: 3-5 reported good absorption into the skin at the time of application.
- Δx: 1-2 reported good absorption into the skin at the time of application.
- x: 0 reported good absorption into the skin at the time of application.

"The Absence of Stickiness on The Skin after Application"

<Assessment Criteria>
- ⊚: 9-10 reported the absence of stickiness after application.
- ◯: 6-8 reported the absence of stickiness after application.
- Δ: 3-5 reported the absence of stickiness after application.
- Δx: 1-2 reported the absence of stickiness after application.
- x: 0 reported the absence of stickiness after application.

TABLE 1

| Ingredients | Example 1 | Example 2 | Example 3 | Example 4 | Example 5 |
|---|---|---|---|---|---|
| (c) Isohexadecane | 10 | 10 | 10 | 10 | 10 |
| Dimethylpolysiloxane (6 cs) | 7 | 7 | 7 | 7 | 7 |
| Isopropyl palmitate | 5 | 5 | 5 | 5 | 5 |
| Mineral oil | 1 | 1 | 1 | 1 | 1 |
| (g) Ethylhexyl methoxycinnamate | 5 | 5 | 5 | 5 | 5 |
| (g) Octocrylene | 5 | 5 | 5 | 5 | 5 |
| Oxybenzone | 1 | 1 | 1 | 1 | 1 |
| (f) Polyether-modified silicone *1 | 2 | 2 | 2 | 2 | 2 |
| (d) Carboxy decyl trisiloxane | 0.3 | 2 | 5 | 1 | 1 |
| Carboxy-modified silicone other than carboxy decyl trisiloxane *2 | — | — | — | — | — |
| Stearic acid | — | — | — | 1 | — |
| Isostearic acid | — | — | — | — | 1 |
| Organically-modified bentonite | 3 | 3 | 3 | 3 | 3 |
| Silicic acid anhydride-containing spherical poly alkyl acrylate | 5 | 5 | 5 | 5 | 5 |
| (e) Hydrophobized zinc oxide *3 | 15 | 15 | 15 | 15 | 15 |
| (e) Hydrophobized titanium dioxide *4 | 7 | 7 | 7 | 7 | 7 |
| (e) Hydrophobized iron oxide *5 | 2 | 2 | 2 | 2 | 2 |
| (a) Ion-exchanged water | Balance | Balance | Balance | Balance | Balance |
| (b) Ethanol | 4 | 4 | 4 | 4 | 4 |
| Glycerin | 2 | 2 | 2 | 2 | 2 |
| Butylene glycol | 5 | 5 | 5 | 5 | 5 |
| Phenoxy ethanol | 0.5 | 0.5 | 0.5 | 0.5 | 0.5 |
| The absence of powdery squeakiness one hour after application | ◯ | ◯ | ⊚ | ◯ | ◯ |
| Good absorption into the skin at the time of application | ⊚ | ⊚ | ◯ | ◯ | ◯ |
| The absence of stickiness on the skin after application | ◯ | ⊚ | ⊚ | ◯ | ◯ |

*1: KF-6017P (Shin-Etsu Chemical Co., Ltd.)
*2: X22-3701E (Shin-Etsu Chemical Co., Ltd.)
*3: FSA62-ZnO(SF) (Daito Kasei Kogyo Co., Ltd.)
*4: ST-485SA (Titan Kogyo Ltd.)
*5: OTS-2 Sachtleben RC402 (Daito Kasei Kogyo Co., Ltd.)

TABLE 2

| Ingredients | Comparative example 1 | Comparative example 2 | Comparative example 3 | Comparative example 4 | Comparative example 5 | Comparative example 6 | Comparative example 7 | Comparative example 8 |
|---|---|---|---|---|---|---|---|---|
| (c) Isohexadecane | 10 | 10 | 10 | — | 10 | 10 | 10 | 10 |
| Dimethylpolysiloxane (6 cs) | 7 | 7 | 7 | 35 | 7 | 7 | 7 | 7 |
| Isopropyl palmitate | 5 | 5 | 5 | — | 5 | 5 | 5 | 5 |
| Mineral oil | 1 | 1 | 1 | — | 1 | 1 | 1 | 1 |
| (g) Ethylhexyl methoxycinnamate | 5 | 5 | 5 | — | 5 | 5 | 5 | 5 |
| (g) Octocrylene | 5 | 5 | 5 | — | 5 | 5 | 5 | 5 |
| Oxybenzone | 1 | 1 | 1 | — | 1 | 1 | 1 | 1 |

TABLE 2-continued

| Ingredients | Comparative example 1 | Comparative example 2 | Comparative example 3 | Comparative example 4 | Comparative example 5 | Comparative example 6 | Comparative example 7 | Comparative example 8 |
|---|---|---|---|---|---|---|---|---|
| (f) Polyether-modified silicone *1 | 2 | 2 | 2 | 2 | 5 | 2 | 2 | 2 |
| (d) Carboxy decyl trisiloxane | — | 0.05 | 10 | — | — | — | — | — |
| Carboxy-modified silicone other than carboxy decyl trisiloxane *2 | — | — | — | — | — | 2 | — | — |
| Stearic acid | — | — | — | — | — | — | 2 | — |
| Isostearic acid | — | — | — | — | — | — | — | 2 |
| Organically-modified bentonite | 3 | 3 | 3 | 3 | 3 | 3 | 3 | 3 |
| Silicic acid anhydride-containing spherical poly alkyl acrylate | 5 | 5 | 5 | 5 | 5 | 5 | 5 | 5 |
| (e) Hydrophobized zinc oxide *3 | 15 | 15 | 15 | 15 | 15 | 15 | 15 | 15 |
| (e) Hydrophobized titanium dioxide *4 | 7 | 7 | 7 | 7 | 7 | 7 | 7 | 7 |
| (e) Hydrophobized iron oxide *5 | 2 | 2 | 2 | 2 | 2 | 2 | 2 | 2 |
| (a) Ion-exchanged water | Balance | Balance | Balance | Balance | Balance | Balance | Balance | Balance |
| (b) Ethanol | 5 | 5 | 5 | 5 | 5 | 5 | 5 | 5 |
| Glycerin | 2 | 2 | 2 | 2 | 2 | 2 | 2 | 2 |
| Butylene glycol | 5 | 5 | 5 | 5 | 5 | 5 | 5 | 5 |
| Phenoxy ethanol | 0.5 | 0.5 | 0.5 | 0.5 | 0.5 | 0.5 | 0.5 | 0.5 |
| The absence of powdery squeakiness one hour after application | x | Δx | ○ | ○ | Δ | x | x | Δ |
| Good absorption into the skin at the time of application | ○ | ○ | x | x | Δx | Δx | Δ | Δx |
| The absence of stickiness on the skin after application | Δx | Δx | ○ | Δ | Δx | x | Δx | Δ |

*1 KF-6017P (Shin-Etsu Chemical Co., Ltd.)
*2: X22-3701E (Shin-Etsu Chemical Co., Ltd.)
*3: FSA62-ZnO(SF) (from Daito Kasei Kogyo Co., Ltd.)
*4: ST-485SA (Titan Kogyo Ltd.)
*5: 0TS-2 Sachtleben RC402 (Daito Kasei Kogyo Co., Ltd.)

The results in Table 1 and Table 2 indicate that, compared with Comparative examples, Examples of the present invention are superior in terms of all the effects, i.e., "the absence of powdery squeakiness one hour after application", "good absorption into the skin at the time of application", and "the absence of stickiness on the skin after application".

Formulation examples of the water-in-oil emulsified skin cosmetic the present invention are shown below.

Example 6

Sunscreen Cream

| | Ingredient | wt % |
|---|---|---|
| (1) | (e) Hydrophobized zinc oxide | 20 |
| (2) | (e) Hydrophobized titanium dioxide | 2 |
| (3) | (g) Ethylhexyl methoxycinnamate | 7 |
| (4) | (c) Decamethylcyclopentasiloxane | 10 |
| (5) | Isopropyl myristate | 5 |
| (6) | Mineral oil | 1 |
| (7) | (d) Carboxy decyl trisiloxane | 2 |
| (8) | Methylsiloxane network polymer | 5 |
| (9) | (f) Polyether-modified silicone | 4 |
| (10) | Organically-modified bentonite | 2 |
| (11) | (a) Ion-exchanged water | Balance |
| (12) | Glycerin | 2.5 |
| (13) | 1,3-Butylene glycol | 5 |
| (14) | (b) Ethanol | 5 |
| (15) | Phenoxyethanol | 0.5 |

Preparation method: (1)-(10) were mixed and dispersed. The water phase, which was (11)-(15) mixed and dissolved, was then added and mixed to obtain the target sunscreen cream.

Example 7

Sunscreen Lotion (Two-layer Type)

| | Ingredient | wt % |
|---|---|---|
| (1) | (c) Decamethylcyclopentasiloxane | 20 |
| (2) | (c) Isohexadecane | 10 |
| (3) | Dimethylpolysiloxane (6 cs) | 5 |
| (4) | (f) Polyether-modified silicone | 2 |
| (5) | (d) Carboxy decyl trisiloxane | 0.5 |
| (6) | (g) Octocrylene | 3 |
| (7) | (g) Ethylhexyl methoxycinnamate | 5 |
| (8) | (e) Hydrophobized zinc oxide | 12 |
| (9) | (e) Hydrophobized titanium dioxide | 5 |
| (10) | Poly methyl methacrylate spherical powder | 3 |
| (11) | Cross-linked silicone/network silicone block copolymer | 3 |
| (12) | (a) Ion-exchanged water | Balance |
| (13) | 2-Amino-2-methyl-1,3-propanediol | 1 |
| (14) | Phenylbenzimidazolesulfonic acid | 2 |
| (15) | Glycerin | 2 |
| (16) | 1,3-Butylene glycol | 3 |
| (17) | Paraben | 0.2 |
| (18) | (b) Ethanol | 5 |

Preparation method: (1)-(11) were mixed and dispersed. The water phase, which was (12)-(18) mixed and dissolved, was then added and mixed to obtain the target sunscreen lotion.

Example 8

Sunscreen Lotion (Two-layer Type)

| | Ingredient | wt % |
|---|---|---|
| (1) | (c) Isododecane | 17 |
| (2) | Dimethylpolysiloxane (6 cs) | 5 |

-continued

| | Ingredient | wt % |
|---|---|---|
| (3) | Glyceryl tri-(caprylate-caprate) | 5 |
| (4) | (d) Carboxy decyl trisiloxane | 3 |
| (5) | (f) Polyether-modified silicone | 2 |
| (6) | Organically-modified bentonite | 0.4 |
| (7) | Organopolysiloxane elastomer spherical powder | 10 |
| (8) | (e) Hydrophobized zinc oxide | 15 |
| (9) | (e) Hydrophobized titanium dioxide | 7 |
| (10) | (a) Ion-exchanged water | Balance |
| (11) | Tranexamic acid | 2 |
| (12) | EDTA | 0.2 |
| (13) | Xylitol | 3 |
| (14) | 1,3-Butylene glycol | 5 |
| (15) | Phenoxyethanol | 0.5 |
| (16) | (b) Ethanol | 3 |

Preparation method: (1)-(9) were mixed and dispersed. The water phase, which was (10)-(16) mixed and dissolved, was then added and mixed to obtain the target sunscreen lotion.

INDUSTRIAL APPLICABILITY

According to the present invention, it is possible to provide a water-in-oil emulsified skin cosmetic into which one, two, or more powders selected from a group consisting of hydrophobized titanium dioxide, hydrophobized zinc oxide, and hydrophobized iron oxide, are blended wherein powdery squeakiness (tactile sensation of a lack of smoothness) on the skin over time after application is suppressed, absorption into the skin at the time of application is improved, and the absence of stickiness after application on the skin is improved.

The water-in-oil emulsified skin cosmetic of the present invention is particularly useful as a sunscreen cosmetic having a superior texture.

The invention claimed is:

1. A water-in-oil emulsified skin cosmetic comprising the following ingredients (a) through (f):
 (a) Water: 5-50 wt %
 (b) Ethanol: 1-20 wt %
 (c) Volatile oil component: 2-50 wt %
 (d) Carboxy decyl trisiloxane represented by the following formula (1): 0.1-5 wt %

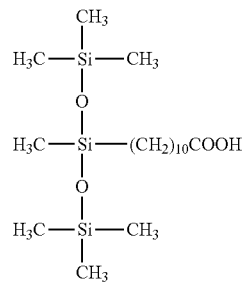

(e) One, two or more selected from the group consisting of hydrophobized titanium dioxide, hydrophobized zinc oxide, and hydrophobized iron oxide: 2-50 wt %, and
 (f) Emulsifying agent;
 wherein the ingredient (d) is dissolved in an oil phase of the water-in-oil emulsified skin cosmetic.

2. The water-in-oil emulsified skin cosmetic of claim 1 wherein the ingredient (f) is polyether-modified silicone.

3. The water-in-oil emulsified skin cosmetic of claim 1, additionally comprising (g) an ultraviolet absorbent.

4. The water-in-oil emulsified skin cosmetic of claim 2, additionally comprising (g) an ultraviolet absorbent.

* * * * *